United States Patent [19]
Jacobson et al.

[11] Patent Number: 5,646,316
[45] Date of Patent: Jul. 8, 1997

[54] BILE ACID INHIBITORS OF METALLOPROTEINASE ENZYMES

[75] Inventors: Alan R. Jacobson, Somerville; Douglas G. Gabler, Cambridge; Jozef Oleksyszyn, Arlington, all of Mass.

[73] Assignee: OsteoArthritis Sciences, Inc., Cambridge, Mass.

[21] Appl. No.: 430,129

[22] Filed: Apr. 25, 1995

Related U.S. Application Data

[63] Continuation of Ser. No. 224,427, Apr. 8, 1994, abandoned.
[51] Int. Cl.$^6$ .................................. C07J 9/00; C07J 41/00
[52] U.S. Cl. ..................... 552/554; 552/515; 552/521; 552/523; 552/524; 540/106; 540/107; 540/112; 540/113; 540/120
[58] Field of Search ........................... 552/554; 540/112, 540/120

[56] References Cited

U.S. PATENT DOCUMENTS

| | | | |
|---|---|---|---|
| 4,220,598 | 9/1980 | Hixson, Jr. et al. | 552/524 |
| 4,681,876 | 7/1987 | Marples et al. | 514/182 |
| 4,957,910 | 9/1990 | Sutton et al. | 514/182 |
| 5,338,837 | 8/1994 | Kahne | 540/106 |

FOREIGN PATENT DOCUMENTS

| | | |
|---|---|---|
| WO90/13298 | 11/1990 | WIPO. |
| WO93/09090 | 5/1993 | WIPO. |
| WO94/00126 | 1/1994 | WIPO. |

OTHER PUBLICATIONS

Kramer, et al., "Bile Acid Derivatives, a Process for their Production and Their Use as Medicines," *Chemical Abstracts*, 115:72019d (1991), EP 417,725.

Kramer, et al., "Bile Acid Derivatives a Process for their Preparation and Their Use as Medicines," *Chemical Abstracts*, 117:171824k (1991), EP 489,423.

G. Damilano, "Choleretic Bile Acid Derivatives—Prepared By Reaction with Amino Acid or Oligo-peptide," World Patent Index, Accession No. 84–264152/43, DE 1 618 265. Abstract, 1967.

M. Nakanishi et al., "Aminopeptidase M from Human Liver. I. Solubilization, Purification, and Some Properties of the Enzyme," *J. Biochem.*, 106:818–825 (1989).

M. Nakanishi et al., "Aminopeptidase M from Human Liver. II. Kenetic Analysis of Inhibition of the Enzyme by Bile Acids," *J. Biochem.*, 106:826–830 (1989).

CA 92:128055 (1979).

CA 109:79724, Elstner, E., DE 3623255, 1988.

CA 89:123042, Grady et al, J. Pharmacol. Exp. Ther., 1978, 205(3); 757–765.

CA 52:7399a, Shimizu et al, J Biochem. 45, 13–16, 1958.

*Primary Examiner*—Rebecca Cook
*Attorney, Agent, or Firm*—Hamilton, Brook, Smith & Reynolds, P.C.

[57] ABSTRACT

The present invention relates to a bile acid derivative, which comprises a bile acid derivatized at the carboxyl group with a hydroxamic acid or hydroxamate ester. The carboxyl group in the bile acid compound can also be derivatized with an amino acid or oligopeptide, whose C-terminus is derivatized with a hydroxamic acid or a hydroxamate ester. The present invention also relates to a method of use of a bile acid or a bile acid derivative to inhibit a metalloproteinase enzyme, comprising contacting a metalloproteinase with an effective amount of a bile acid or bile acid derivative. In another embodiment, the present invention further relates to a method of use of a bile acid or bile acid derivative to therapeutically treat a disease, which is ameliorated by inhibiting a metalloproteinase enzyme. In this method, a therapeutically effective amount of a bile acid, a bile acid derivative or physiologically acceptable salts thereof, is administered to a human or other mammal.

5 Claims, No Drawings

BILE ACID INHIBITORS OF METALLOPROTEINASE ENZYMES

This application is a continuation of application Ser. No. 08/224,427 filed on Apr. 8, 1994, abandoned which is incorporated herein by reference in its entirety.

Metalloproteinases are enzymes which are responsible for the breakdown of extracellular matrix. Such metalloproteinase enzymes include stromelysin, human fibroblast collagenase, human neutrophil collagenase, human sputum collagenase, matrilysin, and gelatinase.

The inhibition of metalloproteinases has been found to have importance in mediating the symptoms of a number of diseases, including the metastasis of tumor cells (Reich et al., *Cancer Res.*, 48:3307–3312 (1988)); rheumatoid arthritis (Mullins et al., *Biochem. Biophys. Acta.*, 695:117–214 (1983); Brinckerhoff, *Arthritis and Rheumatism*, 34:1073–1075 (1991) and osteoarthritis (Woessner, *FASEB J.*, 5:2145–2154 (1991). Other conditions characterized by uncontrolled matrix metalloproteinase activity include periodontal disease, various ulcerated conditions and epidermolysis bullosa. (Johnson et al., *Enzyme inhibition*, 2:1–22 (1987).

Treatments for most of the these diseases have generally been less than adequate. Consequently, there exists a need for a method to effectively inhibit metalloproteinase enzymes or to therapeutically treat a disease associated with uncontrolled proteolysis by metalloproteinases, such as osteoarthritis, rheumatoid arthritis, ulcerations and tumor metastasis.

SUMMARY OF THE INVENTION

The present invention relates to matrix metalloprotease inhibitors comprising bile acid derivatives and methods of use thereof. Suitable bile acid derivatives include bile acids such as lithocholic acid, chenodeoxycholic acid and cholic acid which are functionalized at the carboxyl group with a hydroxamic acid, a hydroxamate ester or an amino acid or oligopeptide whose C-terminus is functionalized with a hydroxamic acid or a hydroxamate ester. The present invention also relates to novel bile acid derivatives and methods of use thereof.

The present invention also relates to a method of use of a bile acid or a bile acid derivative of this invention to inhibit at least one matrix metalloproteinase. A suitable bile acid derivative for this method of use includes a bile acid functionalized at the carboxyl group with a hydroxamic acid, a hydroxamate ester, an amino acid or an oligopeptide. The amino acid or oligopeptide can also be functionalized at the C-terminus. This method of use comprises contacting a matrix metalloproteinase with an effective amount of a bile acid or a bile acid derivative.

The present invention further relates to a method of use of a bile acid or bile acid derivative of this invention to therapeutically treat a disease, which is ameliorated by inhibiting a metalloproteinase, comprising administering a therapeutically effective amount of a bile acid or bile acid derivative, or physiologically acceptable salts thereof, to a host.

The advantages of this invention are numerous. For example, the bile acids and bile acid derivatives of this invention are useful in inhibiting the action of many metalloproteinase enzymes and thus, in treating diseases affected by metalloproteinase proteolysis.

DETAILED DESCRIPTION OF THE INVENTION

The present invention relates to bile acid derivatives and methods of use thereof, wherein said bile acid derivatives are represented by the following structural formula:

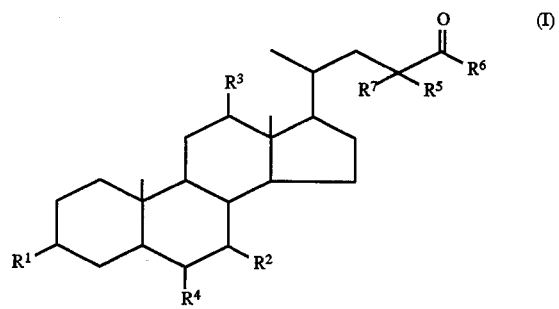

In the novel compositions of this invention, $R^1$, $R^2$, $R^3$ and $R^4$ are each independently selected from the group consisting of H, OH, $OR^5$, $SR^5$, $S(O)R^5$, $S(O)_2R^5$, $S(O)_2OR^5$, and $NHR^5$.

$R^5$ is selected from the group consisting of alkyl, substituted alkyl, aryl, substituted aryl, heteroaryl and substituted heteroaryl.

$R^6$ is:

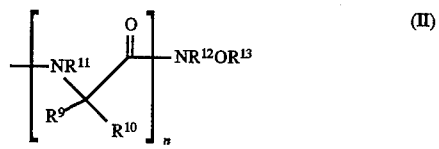

while n is zero or a positive integer.

$R^7$, $R^8$, $R^9$, $R^{10}$, $R^{11}$, $R^{12}$ and $R^{13}$ are each independently selected from the group consisting of hydrogen, substituted alkyl, aryl, substituted aryl, heteroaryl and substituted heteroaryl.

An alkyl moiety, as defined herein, is any straight, cyclic or branched chain C1–C15 hydrocarbon. The hydrocarbon can be monounsaturated, polyunsaturated or completely saturated. Preferably, the hydrocarbon contains from 1 to about 10 carbons. A substituted alkyl group refers to an alkyl group substituted with one or more aryl, substituted aryl, heteroaryl, substituted heteroaryl or functional groups such as hydroxy, alkoxy, aryloxy, amino, substituted amino, thiol, substituted thiol, halo, carbonylbenzyloxy (CBZ) and N-tert-butoxycarbonyl.

An aryl group is phenyl or any polycyclic aromatic hydrocarbon. Suitable aryl groups include, for example, phenyl, naphthyl and anthracyl. A heteroaryl group, as defined herein, is any aryl group which contains one or more heteroatoms such as oxygen, sulfur or nitrogen. Examples of suitable heteroaryl groups include, but are not limited to pyridyl, benzothiophene, indole, quinoline and phenothiazine. A substituted aryl or heteroaryl group refers to an aryl or heteroaryl group substituted with one or more alkyl, substituted alkyl, aryl, heteroaryl, or functional groups such as hydroxy, alkoxy, aryloxy, amino, substituted amino, thiol, substituted thiol, halo, carbonylbenzyloxy (CBZ) and N-tert-butoxycarbonyl.

In a preferred embodiment of the present invention $R^1$, $R^2$, $R^3$ and $R^4$ are each independently selected from H or OH, $R^7$ and $R^8$ are H, and $R^6$ is —NHOH, a hydroxamate ester or an amino acid whose C-terminus is substituted with —NHOH or a hydroxamate ester according to Structural Formula II. A hydroxamate ester is —NHO(alkyl), —NHO (substituted alkyl), —NHO(heteroaryl), —NHO(substituted heteroaryl), —NHO(aryl) or —NHO(substituted aryl).

When $R^6$ is a substituted amino acid, $R^9$ and $R^{11}$ are each H and $R^{10}$ is the side chain of an amino acid. As defined herein, a side chain of an amino acid consists of R, wherein the structure of an amino acid is NH₂—CHR—COOH. For example, the side chain of cysteine would be —CH₂SH. Examples of suitable amino acids include both steroisomers of glycine, alanine, β-leucine, valine, leucine, isoleucine, phenylglycine, p-hydoxyphenylglycine, tyrosine, histidine, tryptophan, homophenylalanine, serine, threonine, cysteine, homocysteine, homoserine, arginine, lysine, methionine, glutamatic acid, aspartic acid, glutamine, asparagine, proline, and hydroxyproline. Preferred amino acids include (L)-leucine, (D)- or (L)-phenylalanine, (D)- or (L)-homophenylalanine, β-(L)-leucine and (L)-tryptophane.

In an even more preferred embodiment of the present invention, $R^1$ is OH, $R^2$ is H or OH, $R^3$ is H, $R^4$ is H and $R^6$ is —NHOH, —NHO(benzyl), (D)- or (L)-phenylalanine hydroxamic acid, (L)-leucine hydroxamic acid, (L)-tryptophane hydroxamic acid, β-(L)-leucine hydroxamic acid, (D)- or (L)-homophenylalanine hydroxamic acid, (L)-phenylalanyl homocysteine thiolactone or (L)-phenylalanyl-(L)-cysteine ethyl ester.

The conversion of a bile acid to a hydroxamic acid derivative occurs by a two step procedure. A bile acid hydroxamate ester is first prepared by a dicyclohexylcarbodiimide (DCC) mediated coupling of the bile acid with an O-(substituted)hydroxylamine hydrochloride, such as O-benzylhydroxylamine hydrochloride. This is followed by hydrogenation of the hydroxamate ester to yield the hydroxamic acid. Specific reactions are described in Examples 1–6, below.

A bile acid, whose carboxylic acid is derivatized with an amino acid or derivatized amino acid, is prepared by a similar procedure. An amino acid ester or an amino acid O-hydroxamate ester is first coupled to a bile acid by DCC mediated coupling. A hydroxamate ester product can be converted to hydroxamic acids by hydrogenation. Ester products can be converted to carboxylic acids by saponification according to methods well known to those skilled in the art. Subsequent DCC mediated couplings with additional amino acids esters can be used to generate a bile acid derivatized with oligopeptides at the carboxyl group. Specific conditions for performing these reactions are described in Examples 1, 2 and 7–13.

In one embodiment of the method of use of the composition of this invention, a bile acid or a bile acid derivative is used to inhibit at least one matrix metalloproteinase enzyme. Examples of metalloproteinase enzymes which can be inhibited include stromelysin, matrilysin, gelatinase, and collagenases such as human fibroblast collagenase, human neutrophil collagenase, and human sputum collagenase. In this method, a metalloproteinase is contacted with an effective amount of a bile acid or a bile acid derivative. Bile acids are represented by Structural Formula I, wherein $R^6$ is selected from the group consisting of hydroxyl, —NH(CH₂)N(CH₃)₃⁺CH₂CH₂CH₂SO₃ and —NH(CH₂)N(CH₃)₃⁺CH₂CHOHCH₂SO₃. Examples include lithocholic acid, 3-[(3-cholamidopropyl)dimethylammonio)-1-propanesulfonate, 3-[(3-cholamidopropyl)dimethylammonia]-2-hydroxy-1-propanesulfonate, deoxycholic acid, ursodeoxycholic acid, hyodeoxycholic, chenodeoxycholic acid and cholic acid. Bile acid derivatives are represented by Structural Formula I, wherein $R^6$ is selected from the group consisting of hydroxyl ester, substituted or unsubstituted amide, substituted or unsubstituted thioester, substituted or unsubstituted hydroxamic acid, substituted or unsubstituted hydroxamic ester, and

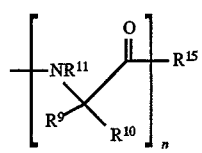

(III)

wherein n is a positive integer. Each of $R^9$, $R^{10}$ and $R^{11}$ are independently selected from the group consisting of hydrogen, alkyl, substituted alkyl, aryl, substituted aryl, heteroaryl and substituted heteroaryl. $R^{15}$ is selected from the group consisting of hydroxyl, hydroxyl ester, substituted or unsubstituted amide, substituted or unsubstituted thioester, substituted or unsubstituted hydroxamic acids, substituted or unsubstituted hydroxamic ester, —NH(CH₂)N(CH₃)₃⁺CH₂CH₂CH₂SO₃⁻, —NH(CH₂)N(CH₃)₃⁺CH₂CHOHCH₂SO₃⁻ and

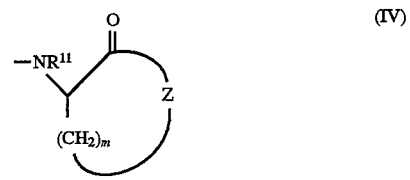

(IV)

wherein Z is oxygen or sulfur and m is an integer from 1 to 5.

For purposes of the present invention, a substituted amide or a substituted thioester refers to an amide or thioester, respectively, which is functionalized with an alkyl, substituted alkyl, aryl, substituted aryl, heteroaryl or substituted heteroaryl. Hydroxyl ester refers to an alkyl, substituted alkyl, aryl, substituted aryl, heteroaryl or substituted heteroaryl ester. A substituted hydroxamic ester or hydroxamic acid refers to a hydroxamate ester or hydroxamic acid in which the nitrogen is substituted with an alkyl, substituted alkyl, aryl, substituted aryl, heteroaryl or substituted heteroaryl group.

Specific examples where at least one matrix metalloproteinase is inhibited in vitro with a bile acid or a bile acid derivative are provided in Examples 13–15. In these examples bile acids and bile acid derivatives are tested in vitro for their ability to inhibit stromelysin, collagenase and/or gelatinases. Inhibition data are provided in Table I as IC₅₀s or percent inhibition at 10 μM of test compound.

Another embodiment of the method of use of a bile acid or bile acid derivative of this invention comprises administering an effective amount of a bile acid or bile acid derivative, or physiologically acceptable salts thereof, to a host to therapeutically treat a disease, which is ameliorated by inhibiting at least one metalloproteinase. Such diseases include, for instance, tumor cell metastasis, rheumatoid arthritis, osteoarthritis, ulcerations and infections resulting from periodontal disease or epidermolysis bullosa.

A host, as defined herein, includes humans and other mammals. An effective amount of a bile acid or bile acid derivative is an amount which brings about an amelioration of a disease process, such as the inhibition of extracellular matrix degradation, without causing an unacceptable amount of side-effects in the host. Examples of effective amounts include between about 0.1 mg/kg to about 100 mg/kg body weight of the individual treated. A preferred amount is from about 1.0 mg/kg to about 20.0 mg/kg.

Specific examples of where the administration of an effective amount of a bile acid or bile acid derivative can bring about the amelioration of a disease process are provided in Examples 16 and 17. In these examples compounds are tested for their ability to inhibit the degradation of extracellular matrix in tissue and cell culture. Inhibition data for the compounds tested in the cell or tissue culture are provided in Table II as $IC_{50}$s or percent inhibition at 50 µM of test compound.

A bile acid or a bile acid derivative can be administered systemically, such as, for example, by intramuscular, intravenous, intra-articular, subcutaneous, or intraperitoneal injection. A bile acid or bile acid derivative can also be administered directly to the treatment site. Alternatively, a bile acid compound can be administered orally, for example, in capsules, suspensions or tablets. A bile acid or bile acid derivative can also be administered as at least one physiologically acceptable salt and/or in conjunction with an acceptable pharmaceutical carrier as part of a pharmaceutical composition for inhibiting extracellular matrix degradation. Standard pharmaceutical formulation techniques may be employed such as those described in Remington's Pharmaceutical Sciences, Mack Publishing Company, Easton, Pa. Suitable pharmaceutical carriers include, for example, cyclodextrans, physiological saline, Hank's solution, Ringer's-lactate and the like.

A bile acid or bile acid derivative of the present invention can be directed to at least one specific location where at least one metalloproteinase is accumulated by using a targeting ligand. For example, to target the bile acid or bile acid derivative to at least one metalloproteinase contained in a specific tissue (e.g., cartilage, ulcerated tissue, tumors, or gums), the compound is conjugated to an antibody or fragment thereof which is immunoreactive with a tissue-specific marker as is understood generally in the preparation of immunotoxins. The targeting ligand can also be a ligand suitable for a receptor which is present on the specific tissue. Any targeting ligand which specifically reacts with a marker for the intended target tissue can be used. Methods for coupling the compounds to the targeting ligand are well known to those skilled in the art.

A bile acid or bile acid derivative can also be utilized in an immunization protocol to obtain an antisera wherein the antisera is immunospecific for said bile acid compound. The bile acid or bile acid derivative is coupled to antigenically neutral carriers such as the conventionally used keyhold limpet hemocyanin (KLH) or serum albumin carriers to form an immunogenic complex. Coupling to carrier is done by methods generally known in the art. Linker compounds, which include long-chain bifunctional aliphatic compounds such as 6-aminocaporic acid, can also be used to effect the coupling and form an immunogenic complex. Homobifunctional and heterobifunctional linkers are available from, for example, Pierce Chemical Company, Rockford, Ill. The resulting immunogenic complex can then be injected into a suitable mammalian subjects, such as mice, rabbits, and the like. A suitable protocol includes the repeated injection of the immunogen in the presence of adjuvants according to a schedule which boosts production of antibodies in the serum. The titers of the immune serum can readily be measured using immunoassay procedures, now standard in the art, employing the compounds as antigens.

An antisera obtained in this method can be used directly or monoclonal antibodies can be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparation formed is then useful in monitoring therapy or prophylaxis regimens involving the compounds of the invention. Suitable samples, such as those derived from blood, serum, urine, or saliva, can be tested for the presence of the administered bile acid compound at various times during the treatment protocol using standard immunoassay techniques which employ the antibody preparations of the invention.

A bile acid or bile acid derivative can also be coupled to a radiolabel, such as the $Te^{99}$ or $I^{131}$ scintigraphic labels, using standard coupling methods. A radiolabeled bile acid or bile acid derivative is then administered to a subject to determine any locations of excess amounts of one or more metalloproteinase in vivo. The ability of a bile acid compound to selectively bind to a metalloproteinase is then used to map the distribution of these enzymes in situ. The techniques can also, of course, be employed in the histological procedures, and the labeled compounds can be used in competitive immunoassays.

At least one bile acid or bile acid derivative can also be coupled to a solid support, such as a separation membrane, a chromatographic support, for example agarose, sepharose, polyacrylamide, or the like, or to a microtiter plate to provide an affinity support which is useful in purifying a matrix metalloproteinase enzyme. The selective binding of the matrix metalloproteinase to the bile acid compound permits the absorption of the desired enzyme and its subsequent elution using, for example, altered ionic strength and/or pH conditions.

The invention will now be further and specifically described by the following examples.

EXEMPLIFICATION

In each synthesis, unless otherwise noted, solutions were concentrated at reduced pressure on a rotary evaporator and thin layer chromatography (TLC) was performed on silica-gel $F_{254}$ (EM Sciences) using methylene chloride 5% methanol. Each bile acid derivative was characterized by high field (300 MHz proton observe) NMR on a Varian Gemini 300, as well as carbon, hydrogen and nitrogen analysis (Galbraith Laboratories, Knoxville, Tenn.).

Lithocholic acid, deoxycholic acid, ursodeoxycholic acid, hyodeoxycholic acid, 3-[(3-cholamidopropyl) dimethylammonio]-2-hydroxy-1-propanesulfonate were purchased from Aldrich Chemical Co. (St. Louis, Mo.) and used without further purification and are hereinafter referred to as Compound 1, 2, 3, 4 and 5 respectively. Chenodeoxycholic acid was purchased from TCI America (Portland, Oreg.) and used without further purification. Chenodeoxycholic acid is hereinafter referred to as Compound 6. Cholic acid and 3-[(3-cholamidopropyl)dimethylammonio)-1-propanesulfonate were purchased from Sigma Chemical Co. (St. Louis, Mo.) and used without further purification. Cholic acid and 3-[(3-cholamidopropyl)dimethylammonio) -1-propanesulfonate are hereinafter referred to as Compounds 7 and 8, respectively.

EXAMPLE 1

Lithocholyl-(L)-Leucine Hydroxamic Acid 200 mg (1.4 mmol) (L)-leucine hydroxamate, 567 mg (1.5 mmol) lithocholic acid and 210 mg (1.4 mmol) hydroxybenzotriazole (HOBt) were added to 20 mL of dimethylformamide (DMF). The solution was allowed to equilibrate for 10 minutes. 310 mg (1.5 mmol) of dicyclohexylcarbodiimide (DCC) were then added, after which the reaction was stirred overnight at room temperature. The mixture then was filtered, diluted with 100 mL $CH_2Cl_2$ and washed successively with 2×40 mL of 5% Hcl, 10% $NaHCO_3$ and brine. The organic layer was dried ($Na_2SO_4$) and concentrated to dryness. The product was purified by preparatory TLC. This product is hereinafter referred to as Compound 9.

EXAMPLE 2

Chenodeoxycholyl-(L)-Leucine Hydroxamic Acid

This compound was prepared as described in Example 1 using 591 mg (1.5 mmol) of chenodeoxycholic acid. This product is hereinafter referred to as Compound 10.

EXAMPLE 3

Lithocholyl-O-Benzylhydroxamate 300 mg (0.08 mmol) of lithocholic acid, 140 mg (0.88 mmol) O-benzylhydroxylamine hydrochloride, 152 µL (0.88 mmol) diisopropylethytamine and (DIEA) and 122 mg (0.80 mmol) HOBt were added to 20 mL of $CH_2Cl_2$. The solution was allowed to equilibrate for 10 minutes, followed by the addition of 180 mg (0.88 mmol) DCC. After then being allowed to stir overnight at room temperature, the reaction mixture was filtered and washed successively with 2×40 mL of 5% HCl, 10% $NaHCO_3$ and brine. The organic layer was dried ($Na_2SO_4$) and concentrated to dryness. The product was purified by preparatory TLC. This product is hereinafter referred to as Compound 11.

EXAMPLE 4

Chenodeoxycholyl-O-Benzylhyroxamate

This compound was prepared as described in Example 3 on a 0.51 mmol scale of chenodeoxycholic acid. This product is hereinafter referred to as Compound 12.

EXAMPLE 5

Lithocholylhydroxamic Acid 150 mg (0.31 mmol) of Compound 7 and 50 mg of 5% Pd on activated carbon were added to 10 mL of MeOH. Debenzylation was carried out overnight at room temperature under a balloon of $H_2$ gas, which was maintained at atmospheric pressure. The reaction was filtered through Celite, concentrated to dryness, and purified by preparatory TLC. This product is hereinafter referred to as Compound 13.

EXAMPLE 6

Chenodeoxycholyhydroxamic Acid

This compound was prepared as described in Example 5, using Compound 8 as starting material. This product is sometimes hereinafter referred to as Compound 14.

EXAMPLE 7

Lithocholyl-(L)-Phenylalanine Hydroxamic Acid 100 g (0.27 mmol) of lithocholic acid, 102 mg (0.29 mmol) (L)-phenylalanine-O-benzylhydroxamate trifluoroacetate, 51 µL (0.29 mmol) DIEA and 41 mg (0.27 mmol) HOBt were added to 20 mL of DMF. The mixture was then allowed to equilibrate 10 minutes, after which 61 mg (0.29 mmol) of DCC were added. The reaction was stirred overnight at room temperature. The reaction was then filtered, diluted with about 75 mL $CH_2Cl_2$ and washed successively with 2×40 mL of 5% HCl, 10% $NaHCO_3$ and brine. The organic layer was dried ($Na_2SO_4$), concentrated to dryness, and used without further purification. The O-benzylhydroxamate was deprotected as in Example 5. After filtering the reaction mixture through Celite and concentrating to dryness, the product was purified by crystallization from $MeOH/H_2O$. The product is sometimes hereinafter referred to as Compound 15.

Phenylalanyl-O-benzylhydroxamate, used hereinabove, was prepared by standard peptide procedures starting from BOC-phenylalanine and O-benzylhydroxylamine. The removal of the BOC group followed using trifluoroacetic acid. (Miklos Bodanszky, "Peptide Chemistry," pp. 69, Springer Verlag (1988)).

EXAMPLE 8

Chenodeoxycholyl-(L)-Phenylalanine Hydroxamic Acid

This compound was prepared as described in Example 7. This product is sometimes hereinafter referred to as Compound 16.

EXAMPLE 9

Lithocholyl-(L)-Tryptophane 1.00 g (2.7 mmol) lithocholic acid, 680 mg (2.9 mmol) (L)tryptophane ethyl ester hydrochloride, 0.4 mL (2.9 mmol) triethylamine ($Et_3N$) and 397 mg (2.7 mmol) of HOBt were added to 40 mL of DMF and allowed to equilibrate 10 minutes. DCC (568 mg (2.9 mmol)) was added and the reaction was stirred overnight at room temperature. The reaction mixture was then filtered, diluted with 150 mL $CH_2Cl_2$ and washed successively with 2×100 mL of 5% citritic acid, 5% $NaHCO_3$, and brine. The organic layer was dried ($Na_2SO_4$) and concentrated to dryness. Saponification of the methyl ester was accomplished by dissolving the ester in 50 mL of MeOH:1N NaOH (10:1) and allowing the reaction to stir at room temperature for about 2 hours, while monitoring for the loss of ester by TLC. The reaction was then concentrated to about 10 mL, diluted with 30 mL $H_2O$ and washed with 3×50 mL $CH_2Cl_2$. The aqueous layer was acidified to a pH of about 2 using 1N HCl and extracted with 4×50 mL of $CH_2Cl_2$. The organic layer was dried ($Na_2SO_4$) and taken to dryness. The product was crystallized from $EtOH/H_2O$. This product is hereinafter referred to as Compound 17.

EXAMPLE 10

Lithocholyl-(L)-Tryptophane Hydroxamic Acid 200 mg (0.36 mmol) of Compound 13, 62 mg (0.39 mmol) O-benzylhydroxylamine hydrochloride, 55 µL (0.39 mmol) $Et_3N$ and 53 mg (0.36 mmol) of HOBt were added to 10 mL of DMF. The solution was allowed to equilibrate 10 minutes, after which 86 mg (0.39 mmol) of DCC were added. The reaction was then allowed to stir overnight at room temperature. Work up and subsequent debenzylation was same as with Example 5. The product was purified by crystallization from $EtOH/H_2O$. This product is hereinafter referred to as Compound 18.

EXAMPLE 11

Lithocholyl-(L)-Phenylalanyl-(L)-Cysteine Ethyl Ester 200 mg (0.53 mmol) lithocholic acid, 115 mg (0.58 mmol) (L)-PheOMe hydrochloride, 105 µL (0.58 mmol) DIEA and 81 mg (0.53 mmol) of HOBt were added to 25 mL $CH_2Cl_2$. The mixture was allowed to equilibrate 10 minutes, after which 120 mg (0.58 mmol) of DCC were added. The reaction was then stirred overnight at room temperature. Work up and saponification was same as with Example 9. The Lithocholyl-(L)-phenylalanine obtained, used without further purification, was dissolved in 20 mL $CH_2Cl_2$ containing 5 mL DMF, 98 mg (0.53 mmol) (L)-cysteine ethyl ester hydrochloride, 105 µL (0.58 mmol) DIEA and 81 mg (0.53 mmol) HOBt. The mixture was allowed to equilibrate for 10 minutes under argon, after which 120 mg (0.58 mmol) DCC were added. The reaction mixture was stirred overnight at room temperature under an atmosphere of argon. The reaction was then filtered and washed successively with 2×40 mL of 5% HCl, 10% $NaHCO_3$, and brine. The organic layer was dried ($Na_2SO_4$) and concentrated to dryness. The product was purified by preparatory TLC. This product is hereinafter referred to as Compound 19.

EXAMPLE 12

Lithocholyl-Phenylalanylhomocysteine Thiolactone

A 100 mg portion (0.19 mmol) of the intermediate Lithocholyl-(L)-phenylalanine, prepared as described in Example 11, was coupled with 50 mg (D,L)-homocysteine thiolactone hydrochloride (0.29 mmol) in 10 mL $CH_2Cl_2$ and 5 mL DMF. The reaction mixture also contained 45 µL (0.29 mmol) $Et_3N$, 30 mg (0.19 mmol) HOBt and 43 mg (0.21 mmol) DCC. The reaction was stirred overnight at room temperature. The reaction was then filtered and washed successively with 2×40 mL of 5% HCl, 10% $NaHCO_3$, and brine. The organic layer was dried ($Na_2SO_4$) and concentrated to dryness, and the product purified by preparatory TLC. This product is sometimes hereinafter referred to as Compound 20.

EXAMPLE 13

Lithocholyl-β-Leucine Hydroxamic Acid

The synthesis of BOC-β-(L)-leucine methyl ester was performed as reported (*J. Med. Chem.* 32:2199, (1988)). The removal of the BOC protecting group using trifluoroacetic acid afforded the TFA salt, which was used without further purification. Coupling with lithocholic acid, and subsequent saponification was performed according to the procedure described in Example 9. The lithocholyl-β-(L)-leucine thus obtained was coupled with O-benzylhydroxylamine according to procedure described in Example 3, and debenzylation to afford lithocholyl-β-(L)-leucylhydroxamic acid was performed according to the procedure described in Example 5. The product was purified by preparatory TLC. This product is sometimes hereinafter referred to as Compound 21.

EXAMPLE 14

Lithocholyl-(D)-Phenylalanine Hydroxamic Acid

Synthesis of this compound was performed according to the procedure in Example 9, using the hydrochloride salt of (D)-phenylalanine methyl ester and coupling with lithocholic acid. Preparation of the hydroxamate followed the general procedures described in Example 10. The final product was purified by preparatory TLC. This product is sometimes hereinafter referred to as Compound 22.

EXAMPLE 15

Cholylhydroxamic Acid

This compound was prepared from cholic acid and O-benzylhydroxamate according to the procedure described in Example 3. Debenzylation and subsequent purification followed the procedure in Example 5. This product is sometimes hereinafter referred to as Compound 23.

EXAMPLE 16

Ursodeoxycholyl-(L)-Leucine Hydroxamic Acid

Preparation of this compound followed the procedure described in Example 1. This compound is sometimes hereinafter referred to as Compound 24.

EXAMPLE 17

Hyodeoxycholyt-(L)-Leucine Hydroxamic Acid

Preparation of this compound followed the procedure described in Example 1. This compound is sometimes hereinafter referred to as Compound 25.

EXAMPLE 18

Deoxycholyl-(L)-Leucine Hydroxamic Acid

Preparation of this compound followed the procedure described in Example 1. This compound is sometimes hereinafter referred to as Compound 26.

EXAMPLE 19

Lithocholyl-(L)-homophenylalanine Hydroxamic Acid

Synthesis of this compound followed the procedure described in Example 9 starting from the hydrochloride salt of (L)-homophenylalanine methyl ester. Formation of the O-benzylhydroxamate, and subsequent debenzylation was as performed according to the procedure described in Example 10. This compound is sometimes hereinafter referred to as Compound 27.

EXAMPLE 20

Lithocholyl-(D)-homophenylalanine Hydroxamic Acid

Synthesis of this compound followed the procedure described in Example 19, starting from the (D)-isomer of homophenylalanine. This compound is sometimes hereinafter referred to as Compound 28.

EXAMPLE 21

Assay of Stromelysin Inhibition Activity

Stromelysin was first activated by trypsin. This was done by preparing a reaction mixture in B-150 (B-150 consists of 150 mM NaCl, 20 mM Tris at pH 7.8 and 0.02% sodium azide) containing a final concentration of 4 µg/mL trypsin, 1.48 µg/mL of stromelysin, and 3.15 mM $CaCl_2$. The reaction was incubated for 30 minutes at 37° C. and then quenched by adding soybean trypsin inhibitor to a final concentration of 43.6 µg/mL. $ZnCl_2$ was added to the reaction mixture for a total concentration of 0.24 µM.

Following preparation of the solution of activated stromelysin, assay solutions were prepared for each inhibitor being tested. A control was also prepared. First, 20 nanomoles of activated stromelysin (about 45 µL from the solution of activated stromelysin) were aliquotted per assay tube. A 2.5 mM solution in 100% dimethyl sulfoxide (DMSO) was prepared for each inhibitor being tested and 1 µL from each inhibitor solution was added to one of the assay tubes. In addition, 1 µL of 100% DMSO was added to the control assay tube. All assay tubes were then pre-incubated for 5 minutes.

5 µL of a previously prepared 50 µM solution of substrate in 15% DMSO were added to each assay tube. The substrate was a methoxycumarin developed by Knight et al. *FEBS Lett.* 296:263–66 (1992). The tubes were then incubated for 60 minutes, at which time the reaction was stopped with the addition of 750 µL of 0.1M NaAc pH 4.0 buffer.

Substrate hydrolysis was assessed by fluorescence using a slit width of 10:10, excitation at 328 nm and emission at 393 nm. The results of these assays are listed in Table I as percent inhibition at 10 µM of the bile acid provided compound tested or as the $IC_{50}$.

EXAMPLE 22

Assay of Collagenase Inhibition Activity

The assay procedure for collagenase was the same as described in Example 13 for stromelysin except that the trypsin activation was performed for 45 minutes. In addition, the incubation of the assay tubes at 37° C. was only for 45 minutes, and the final enzyme concentration is 6 nm. The results of these assays are provided in Table I as percent inhibition at 10 µM of the compound tested.

EXAMPLE 23

Assay of Gelatinase Inhibition Activity

The assay procedure for gelatinase (72 (Kd) was the same as described in Example 13 for stromelysin except that the trypsin activation was performed for 60 minutes. In addition, the incubation of the assay tubes at 37° C. was for 60 minutes, and the final enzyme concentration was 3 nm. The results of these assays are listed in Table I as percent inhibition at 10 µM of the compound tested.

TABLE I

| Compound | Stromelysin | Collagenase | Gelatinase |
|---|---|---|---|
| 1 | 38 µM | 27% | NA |
| 2 | 23% | ND | ND |
| 3 | 21% | ND | ND |
| 4 | 18% | ND | ND |
| 5 | 15% | ND | ND |
| 6 | NA | 6% | NA |
| 7 | 24% | 21% | 4% |
| 8 | 26% | 22% | NA |
| 9 | 1 µM | 27% | 300 nM |
| 10 | 5 µM | 8% | 27% |
| 11 | 25% | 13% | 21% |
| 12 | 5% | 21% | NA |
| 13 | 56% | 35% | 8 µM |
| 14 | NA | 19% | NA |
| is | 85% | 58% | 47% |
| 16 | 80% | 38% | 23% |
| 17 | ND | ND | 5% |
| 18 | 90% | 35% | 41% |
| 19 | 2 µM | 33% | 47% |
| 20 | 57% | 57% | 30% |
| 21 | 3 µM | ND | 7 µM |
| 22 | 1.2 µM | ND | ND |
| 23 | 12% | ND | ND |
| 24 | ND | ND | ND |
| 25 | ND | ND | ND |
| 26 | ND | ND | ND |
| 27 | 90% | ND | ND |
| 28 | 92% | ND | ND |

ND = not determined
NA = not active at the screening dose

The results in Table I indicate that each bile acid compound tested was effective in inhibiting at least one matrix metalloproteinases enzyme.

EXAMPLE 24

Bovine Cartilage Explant Assay

A tissue culture assay was used to measure the ability of the compounds of the present invention to slow the degradation of the extracellular matrix by metalloproteinases. This assay measured the amount of $^{35}$S-glycosaminoglycan ($^{35}$S-GAG) released from labeled bovine cartilage explants.

Knee joints from a 1 to 3 week old calf were obtained immediately after sacrifice from the Abattoir and then transported on ice. The intact joints were washed well with tap water and soaked in 50% (v/v) Povidine iodine solution, obtained from Burre National, Inc., Baltimore, Md. All subsequent steps were performed in a laminar flow tissue culture hood using standard sterile technique. The joint was immobilized in a shank holder and the joint capsule was cut open to expose the articular cartilage. Cartilage explant plugs, approximately 15 mg wet weight, were removed from the flat articulating surfaces in the lower-most region of the knee joint using a sterile steel cork-borer and collected in a 250 mL roller bottle containing about 100 mL fresh Delbecco's minimum essential medium (DMEM), obtained from Gibco BRC, Life Technologies, Gaithersburg, Md., containing 4.5 g/1 (D)-glucose and (L)-glutamine, without sodium pyruvate. The fresh media also contained enough Hepes buffer and sodium bicarbonate such that the pH was about 7.4. The media was then further supplemented just before use with 100 units Penicillin, 100 µg Streptomycin, and 50 µg (L)-ascorbic acid per mL of medium.

Once collected, the explant plugs were washed four times with 50 mL fresh DMEM. The plugs were then placed in the incubator for a minimum of 1 hour to equilibrate, before proceeding to make disks from the articulating surface of each plug. A 1 mm thick disk was sliced from individual plugs from the end that was the articulating surface of the joint. The plug was held steady in the sterile template (4 mm diameter×1.5 mm deep) using sterile forceps. A scalpel blade was used to carefully slice off the disk. Only the superficial articulating surface responded well in culture.

Individual disks obtained were transferred to a tissue culture flask containing about 100 mL fresh media. The flask containing the disks was placed in an incubator at 37° C. (with 5% $CO_2$, 95% air) and allowed to equilibrate overnight and at least one additional day before labeling. When ready to label, the old media was replaced with 50 mL fresh media containing about 500 µCi $^{35}$S-Sodium Sulfate. The plugs were labeled in bulk for about 48 hours. The next morning, the "hot" media was removed and replaced with fresh "cold" media. The disks were again allowed to equilibrate overnight before being used for actual experiments.

The media in which the disks were stored was changed immediately prior to performing the assay. The disks were then returned to the incubator until the test media and the two control media had been prepared. The test media consisted of a bile acid or bile acid derivative (50 µM) being tested for its ability to inhibit extracellular matrix degradation and concomitant recombinant human Interleukin rhIL-1α (5 ng/mL) in fresh DMEM solution. The control media were identical to the test media, except that the first control media lacked rhIL-1α and the second control media lacked an inhibitor, i.e. a bile acid or bile acid derivative. 250 µL of each of the test and control media were transferred to separate 96-well TC plates. Flamed forceps were used to transfer a disk from the incubator to each 96-well TC plates that had been filled with either the test media or one of the two control media.

The TC plates were then placed in the incubator and cultured for 3–4 days (initial incubation with rhIL-1α alpha takes at least 3 days to stimulate endogenous metalloproteinases). A 50 µL aliquot of media from each TC plate was saved and counted. The rest of the media was removed with a suction device.

The cartilage disks from each TC plate were also saved for counting. The disks were removed with forceps and placed in microcentrifuge tubes and then dissolved in 250 µL of full strength Formic Acid. The tubes were capped and placed at 65°–70° C. in a block-heater for 4–6 hours. A 50 µL aliquot was then counted.

The percent $^{35}$S-GAG release is calculated as follows:

$$\% \ ^{35}S\text{-}GAG \ release = \{(cpm_{medium})/(cpm_{medium} + cpm_{explant})\} \times 100\%$$

The percent inhibition at 50 µM of extracellular matrix damage in cartilage explant was calculated as follows:

$$\% \ Inhibition = \frac{(A-B)-(C-B)}{(A-B)} \times 100,$$

wherein

A=% GAG release induced by rhIL-1α;

B=% GAG release in the absence of rhIL-1α; and

C=% GAG release in the presence of rhIL-1α plus 50 µM of compound.

The percent inhibition, of extracellular matrix damage, for 50 µM of each bile acid compound tested, is provided in Table II below.

EXAMPLE 25

Chondrocyte Cell Culture Matrix Breakdown Assay

Isolation of the Cartilage

A cell culture assay was used to measure the ability of compounds to slow the degradation of the extracellular matrix by a metalloproteinase. This assay measured the amount $^{35}$S released from chondrocytes grown in a media with $^{35}$S labeled sodium sulfate. The cell culture assay was carried out as follows:

Two or three 1 to 3 week old calf joints were obtained from an abattoir. The proximal end of the shank was at about 4–5" long to facilitate immobilization in the holder. The joint was kept cool and transported on ice. The exterior of the intact joints was washed well with a suitable anti-microbial soap, rinsed clean with warm water, rinsed in betadine and then finally rinsed with 70% ethanol. Up to this point all steps were done in a manner to ensure that the joint was kept as clean as possible. All subsequent steps were performed in a sterile field (i.e., in a Edgeguard laminar flow tissue culture hood). The joint was immobilized and the synovial fluid was aspirated with a needle and syringe. The joint was then cut open to expose the articular cartilage using a #21 scalpel. Using locking hemostats, forceps and a #15 scalpel, the cartilage was excised in full thickness pieces. Care was taken not to cut too deep because bleeding would have occurred if the subchondral bone, was penetrated. The cartilage pieces were placed into a 50 mL centrifuge tube containing 25 mL of Delbecco's phosphate buffered saline (D-PBS) supplemented with 1% antibiotic solution (penicillin, streptomycin and fungizone; GIBCO/BRL). The slices from each joint were then placed into separate 50 mL centrifuge tubes. The D-PBS was decanted and replaced with 25 mL of fresh D-PBS supplemented with antibiotics and subsequently agitated gently.

Enzymatic Digestion

The cartilage pieces were transferred to a fresh 50 mL centrifuge tube and rinsed once more with 25 mL of D-PBS minus antibiotics. An enzymatic digestion solution containing 1 mg/mL of hyaluronidase in serum-free 1:1 DMEM/Ham's F-12 (DMEM/F12) was prepared. This solution was filter sterilized with 0.22 mm Milex—GV filter and kept on ice until ready to use. The cartilage pieces were digested with approximately 5 mL of hyaluronidase solution per joint for 2×15 minutes at 37° C. in the 50 mL centrifuge tube with gentle agitation at the 15 minute mark. This procedure removed residual hyaluronic acid from the surface of the chips. The enzymatic digestion solution was then aspirated and the cartilage pieces were rinsed with 25 mL of D-PBS.

A second enzymatic digestion solution containing 2.5 mg trypsin and 2 mg collagenase P per mL serum-free DMEM/F12 was prepared. This solution was also filter sterilized with a 0.22 mm Millex—GV filter and kept on ice until ready to use. The cartilage pieces were digested with approximately 5 mL of trypsin: collagenase solution per joint for 2×15 minutes at 37° C. in the 50 mL centrifuge tube with gentle agitation at the 15 minute mark. This procedure removed the synovial fibroblasts and any adherent connective tissue from the surface of the chips. The enzymatic digestion solution was then carefully removed and saved and the cartilage pieces were rinsed with 25 mL of D-PBS.

A third enzymatic solution containing 2 mgs of collagenase P (BMB) per mL serum-free DMEM/F12 was prepared. This solution was filter sterilized with a 0.22 mm Millex—GV filter and kept on ice until ready to use. The pre-digested cartilage pieces were finally digested with approximately 20 mL of enzymatic digestion solution per joint for 5–6 hours at 37° C. in a Bellco stirring digestion flask, at which point the cartilage was fully digested away.

Culture and Growth of Isolated Chondrocytes

The enzymes in the synovial fibroblast and chondrocyte digest were neutralized by addition of an equal volume of DMEM/F12 supplemented with 5% fetal bovine serum. Fibroblasts were plated in DMEM at a cellular density of 6.6×10$^3$ cells per cm$^2$. The chondrocytes were recovered by filtration through a 70 mm nylon Cell Strainer (Falcon Labware, Inc.), which removed the remaining undigested tissue pieces and clumps of cells. Chondrocytes were then collected by centrifugation at 1000×g for 10 minutes at room temperature. The chondrocytes were then resuspended in 40 mL of DMEM/F12 supplemented with 5% fetal bovine serum. A 200 µL aliquot in 20 mL of isoton was quantitated in a Coulter counter. Chondrocytes were diluted with 1:1 (v/v) DMEM/F-12 supplemented with 5% fetal bovine serum to a density of 2×10$^4$ cells per cm$^2$ of culture surface. This density allowed the cells to be at confluence as soon as they are plated. Four days later the cells were again fed with media. This time period ensured the attachment of the chondrocytes to the plastic well.

Chondrocytes were plated at 8×10$^4$ cells/2 cm$^2$ per well with 0.5 mL of 1:1 (v/v) DMEM/F12 supplemented with 10% fetal bovine serum in 24 well plates and incubated for 4 days. The cultures were then fed on days 4, 7, 11, 14, 18 and 21 with 0.5 mL/well of DMEM/F12 plus 10% fetal bovine serum. At this time the cells were densely confluent and have developed a three-dimensional extracellular matrix.

Radiolabel & Chase of Chondrocytes

On day 22, the wells are rinsed 2×1 mL with D-PBS and incubated for 30 minutes in 0.5 mL of DMEM/F12 per well. This starve media was removed, replaced with 0.5 mL/well of DMEM/F23 plus 10 µCi $^{35}$S labeled sodium sulfate per well and incubated for 48 hours at 37° C. On day 24, the labeling media is removed. The wells were then re-fed with 0.5 mL of DMEM/F12 plus 10% fetal bovine serum. The cultures were "chased" with cold sulfate (in the tissue culture media) for two more days and on day 26 were re-fed with 0.5 mL of fresh DMEM/F12 plus 10% fetal bovine serum.

Experimental Addition and Harvest

On day 27, the wells were rinsed 2×1 mL with D-PBS and incubated for 22–24 hours with 0.5 mL/well of serum free DMEM/F12, 1 ng/ml of rhIL-1α, plus inhibitors at the desired concentrations, i.e. the bile acid or bile acid derivative. The wells were carefully rinsed to remove any residual fetal bovine serum which could affect the final results. A first control was run in which the assay was carried out in the absence of inhibitor. A second control was also run in which the assay was carried out in the absence of inhibitor and rhIL-1α. On day 28 the 0.5 mL of media was removed and counted in a mini-vial with 4 mL of scintillation fluid. The cell layer was rinsed 1×1 mL with D-PBS and harvested with 0.5 mL of 1× trypsin-EDTA (purchased from Gibco-BRC, Life Technologies, Gaithersburg, Md.) (incubated for at least 15–20 minutes) for scintillation counting as before. The data is expressed as percent radiolabel released in the media of the total according to the formula:

$$\% \text{ release} = \frac{cpm_{media}}{(cpm_{media}) + (cpm_{cell\ layer})}$$

The average percent release is used to determine a percent inhibition according to the following formula:

$$\% \text{ Inhibition} = \frac{A - B}{C - B} \times 100,$$

wherein,

A=% release in presence of Compound;

B=% release in control; and

C=% release in presence of rhIL-1α.

The percent inhibition at 50 μM or IC$_{50}$ value for each compound tested in the tissue culture and cell culture assay is given in Table II below.

TABLE II

| Compound | Cell Culture | Tissue Culture |
|---|---|---|
| 1 | 95% | 68% |
| 2 | −14% | ND |
| 3 | 5% | ND |
| 4 | 7% | ND |
| 5 | 35% | ND |
| 6 | NA | 23% |
| 7 | NA | −90% |
| 8 | 2% | −120% |
| 9 | 43% | 84% |
| 10 | 80 μM | 85% |
| 11 | NA | NA |
| 12 | 64% | 6% |
| 13 | 20 μM | 44% |
| 14 | 77% | NA |
| 15 | 38% | 54% |
| 16 | 85% | 94% |
| 17 | ND | 8% |
| 18 | ND | 3% |
| 19 | 4% | 32% |
| 20 | 16% | −13% |
| 21 | 88% | ND |
| 22 | 5% | ND |
| 23 | −20% | ND |
| 24 | ND | ND |

TABLE II-continued

| Compound | Cell Culture | Tissue Culture |
|---|---|---|
| 25 | ND | ND |
| 26 | ND | ND |
| 27 | ND | ND |
| 28 | ND | ND |

ND = not determined
NA = not active at the screening dose

Equivalents

Those skilled in the art will know, or be able to ascertain using no more than routine experimentation, many equivalents to the specific embodiments of the invention described herein. These and all other equivalents are intended to be encompassed by the following claims.

The invention claimed is:

1. A matrix metalloproteinase inhibitor represented by the following structural formula:

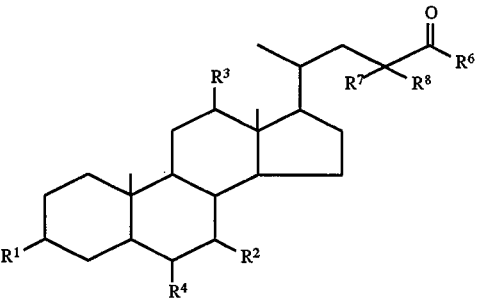

wherein:

a) $R^1, R^2, R^3$ and $R^4$ are each independently selected from the group consisting of H, OH, OR$^5$, SR$^5$, S(O)R$^5$, S(O)$_2$R$^5$, S(O)$_2$OR$^5$ and NR$^5$;

b) $R^5$ is selected from the group consisting of alkyl, substituted alkyl, aryl, substituted aryl, heteroaryl and substituted heteroaryl;

c) $R^6$ is;

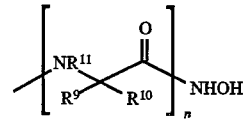

d) $R^7$, $R^8$, $R^9$ and $R^{11}$ are each independently selected from the group consisting of alkyl, substituted alkyl, aryl, substituted aryl, heteroaryl and substituted heteroaryl;

e) $R^{10}$ is selected from the group consisting of alkyl, substituted alkyl, aryl, substituted aryl, heteroaryl, substituted heteroaryl and the side chain of an amino acid selected from the group consisting of alanine, β-leucine valine, leucine, isoleucine, phenylglycine, p-hydoxyphenylglycine, tyrosine, histidine, tryptophan, homophenylalanine, serine, threonine, cystsine, homocysteine, homoserine, arginine, lysine, methionine, glutamatic acid, aspartic acid, glutamine, asparagine, proline, and hydroxyproline; wherein aryl is selected from the group consisting of phenyl, naphthyl and anthracyl;

heteroaryl is selected from the group consisting of pyridyl, benzothiophene, indole, quinoline and phenothiazine;

substituted alkyl has one or more substituents selected from the group consisting of hydroxy, alkoxy, aryloxy, amino, thiol, halo, carbonylbenzyloxy (CBZ), N-tert-butoxycarbonyl, aryl, substituted aryl, heteroaryl and substituted heteroaryl; and substituted aryl and substituted heteroaryl each independently have one or more substituents selected from the group consisting hydroxy, alkoxy, aryloxy, amino, thiol, halo, carbonylbenzyloxy, N-tert-butoxycarbonyl, alkyl, aryl, and heteroaryl; and f) n is one or two.

2. The matrix metalloproteinase inhibitor of claim 1 wherein:

a) $R^1$ is OH;
b) $R^2$ is H or OH;
c) $R^3$, $R^4$, $R^7$, $R^8$, $R^9$ and $R^{11}$ are each H;
d) n is 1; and
e) $R^{10}$ is a side chain of an amino acid.

3. The matrix metalloproteinase inhibitor of claim 2 wherein $R^{10}$ is the side chain of an amino acid selected from the group consisting of (L)-tryptophane, β-(L)-leucine, (D)-phenylalanine, (L)-homophenylalanine, (D)-homophenylalanine, (L)-phenylalanine and (L)-leucine.

4. The matrix metalloproteinase inhibitor of claim 1 wherein:

a) $R^1$ and $R^3$ are each OH;
b) $R^2$, $R^4$, $R^7$, $R^8$, $R^9$ and $R^{11}$ are each H;
c) n is 1; and
d) $R^{10}$ is the side chain of an amino acid.

5. The matrix metalloproteinase inhibitor of claim 1 wherein:

a) $R^1$ and $R^4$ are each OH;
b) $R^2$, $R^3$, $R^7$, $R^8$, $R^9$ and $R^{11}$ are each H;
c) n is 1; and
d) $R^{10}$ is the side chain of an amino acid.

* * * * *